United States Patent
Houston et al.

(10) Patent No.: US 7,112,220 B2
(45) Date of Patent: Sep. 26, 2006

(54) VALVE

(75) Inventors: Graeme J Houston, Perth (GB); Peter A Stonebridge, Perth (GB); John Bruce Cameron Dick, Cupar (GB); Robert Gordon Hood, Longforgan (GB)

(73) Assignee: Tayside Flow Technologies Limited, (GB)

( * ) Notice: Subject to any disclaimer, the term of this patent is extended or adjusted under 35 U.S.C. 154(b) by 0 days.

(21) Appl. No.: 10/467,588

(22) PCT Filed: Feb. 7, 2002

(86) PCT No.: PCT/GB02/00538

§ 371 (c)(1),
(2), (4) Date: Jan. 15, 2004

(87) PCT Pub. No.: WO02/062271

PCT Pub. Date: Aug. 15, 2002

(65) Prior Publication Data

US 2004/0117010 A1 Jun. 17, 2004

(30) Foreign Application Priority Data

Feb. 8, 2001 (GB) .................................. 0103076.6

(51) Int. Cl.
*A61F 2/24* (2006.01)
(52) U.S. Cl. ..................... 623/2.12; 623/2.33
(58) Field of Classification Search ............... 623/2.12, 623/2.13, 2.14, 2.17, 2.18, 2.2, 2.21, 2.33
See application file for complete search history.

(56) References Cited

U.S. PATENT DOCUMENTS

| | | | |
|---|---|---|---|
| 3,113,586 A | 12/1963 | Edmark, Jr. et al. | |
| 3,593,343 A | 7/1971 | Viggers | |
| 3,938,197 A | 2/1976 | Milo | |
| 4,556,996 A | 12/1985 | Wallace | |
| 4,643,732 A * | 2/1987 | Pietsch et al. | 623/2.2 |
| 4,775,378 A | 10/1988 | Knoch et al. | |
| 5,099,808 A * | 3/1992 | Matsuura et al. | 123/188.7 |
| 6,051,022 A | 4/2000 | Cai et al. | |
| 6,086,612 A | 7/2000 | Jansen | |
| 6,117,169 A | 9/2000 | Moe | |
| 6,132,364 A | 10/2000 | Rottenberg et al. | |
| 6,174,232 B1 * | 1/2001 | Stoll et al. | 454/184 |
| 2003/0097175 A1 * | 5/2003 | O'Connor et al. | 623/2.17 |

FOREIGN PATENT DOCUMENTS

| | | |
|---|---|---|
| DE | 3207690 A1 | 3/1982 |
| EP | 0601804 A1 | 6/1994 |
| FR | 1464202 A | 11/1966 |
| WO | WO-98/36792 A1 | 8/1998 |
| WO | WO-0048533 A | 8/2000 |
| WO | WO-0134068 A | 5/2001 |

* cited by examiner

*Primary Examiner*—Bruce Snow
(74) *Attorney, Agent, or Firm*—DeMont & Breyer,

(57) ABSTRACT

There is disclosed a heart valve prosthesis having a configuration such that blood flow through it has a helical flow pattern such as to substantially reduce or eliminate turbulence and dead flow regions in the blood flow.

5 Claims, 2 Drawing Sheets

VALVE

This invention relates to valves, and especially, though not exclusively, to one-way valves, more particularly for use in clinical situations and most particularly to heart valve prostheses.

Heart valve prostheses comprise one-way valves which are implanted in place of diseased or defective natural valves and are made of bio-compatible materials such as stainless steel and certain plastics as well as material harvested from other animals, such as pigs. Both flap valves and ball valves are known. Flap valves comprise one or two flexible plastics material flaps seating on a ledge in a valve annulus or on each other. Ball valves have a ball movable in a cage seating against a portion of a valve annulus. Some valves emulate human heart valves by comprising multiple cusps or leaflets.

Heart valve prostheses are designed according to a number of design considerations. One consideration is clearly durability and functionality over a long period of time. Another is ease of implantation, and valves are designed both for open-chest surgery and so-called keyhole surgery avoiding the major trauma of open-chest surgery. By and large, valve materials are smooth and configurations are rounded or streamlined to avoid undue disturbance to the blood flow when open, but limitations of the materials used and the need for suturing in place militate against a perfect replica being made of a natural valve.

It has been proposed to design blood flow tubing, such as vascular prostheses, in such a way as to improve blood flow and reduce turbulence and dead flow areas, where blood vessel lining can be damaged leading to narrowing and occlude flow or even form thromboses. While such improvement is welcome, its beneficial effects can be reduced or even reversed by locations in the vascular system where such improvement is not present.

One such location could be a prosthetic heart valve, which might, despite design measures to the contrary, induce a wholly or partly different flow pattern to that produced by a natural healthy valve, and the manner of attachment may further affect the flow adversely.

The invention provides a heart valve which does not suffer, at least to the same extent as conventional valve, the problems of deleterious flow interference or alteration.

The invention comprises a heart valve having a configuration such that blood flow through it has a helical flow pattern such as to substantially reduce or eliminate turbulence and/or dead flow regions in the blood flow.

The flow pattern may be similar to, if not exactly the same as helical flow patterns observed in normal blood vessels.

The invention can also have impact in valves other than heart valves and in flows of fluid other than blood.

The valve may induce a helical flow in the blood entering and/or leaving the valve.

The valve may have an internal helical configuration.

The valve may be a flap valve, and may then have flap means which, when open, adopt a helical configuration. By "helical" is meant generally, rather than mathematically precisely helical, of course.

A flap valve may have a single flap seated on a helical valve seat, having hinging inclined to the general flow direction. Or it may have a pair of cooperating flaps hinged on skew hinges and twisted to mate in the closed configuration and opening so that they form complementary flow-directing vanes.

A flap valve may have a plurality of cooperating flaps, cusps or leaflets mating in an iris-like configuration and opening so as to form complementary flow-directing vanes, each having hinging inclined to the general flow direction.

The hinging may comprise a defined hinge line formed by a linear thinned portion of flap material, or may comprise a thin flexible region of flap material which arcs smoothly on opening.

The valve may be a ball valve, which may have a valve seat comprising vane means having a helical configuration.

Embodiments of heart valves according to the invention will now be described with reference to the accompanying drawings, in which.

Figure 1:
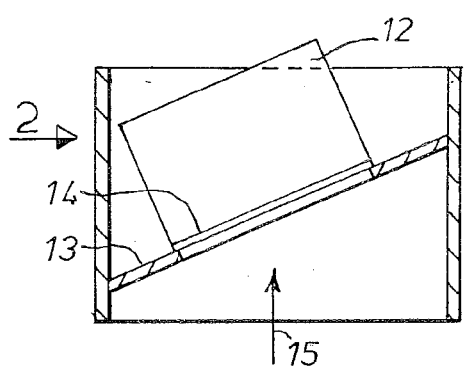
FIG. 1 is a side elevation of a first embodiment.

The drawings illustrate heart valves 11 having a configuration such that blood flow through them has a helical flow pattern such as to substantially reduce or eliminate turbulence and/or dead flow regions in the blood flow.

The valves 11 induce a helical flow in the blood entering and/or leaving the valve, and have an internal helical configuration.

FIGS. 1 to 6 illustrate flap valves 11, having flap means 12 which, when open, adopt a helical configuration. By "helical" is meant generally, rather than mathematically precisely helical, of course. In the drawings, the open position is shown in solid line, the closed position in broken line.

Figure 2:
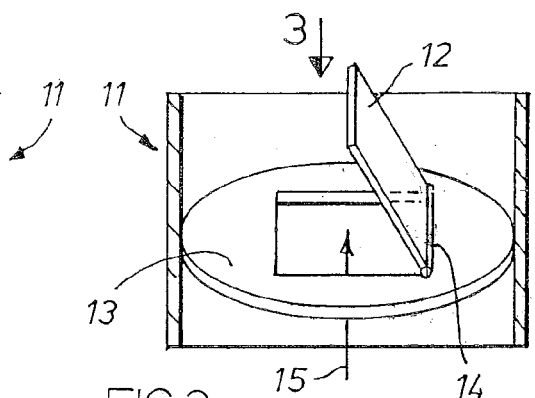
FIG. 2 is an elevation on Arrow 2 of FIG. 1.
Figure 3:
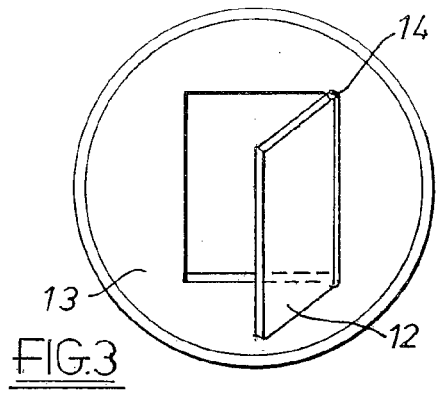
FIG. 3 is a plan on Arrow 3 of FIG. 1.

The valve illustrated in FIGS. 1 to 3 has a single flap 12 seated on a helical valve seat 13 having hinging 14 inclined to the general flow direction, arrow 15. When the valve is open, the flap imparts a rotational element to the flow.

Figure 6:
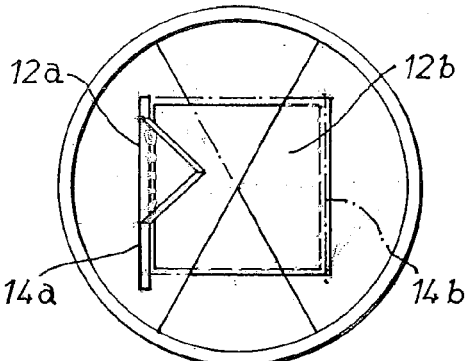
FIG. 6 is a plan on Arrow 6 of FIG. 4.
Figure 4:
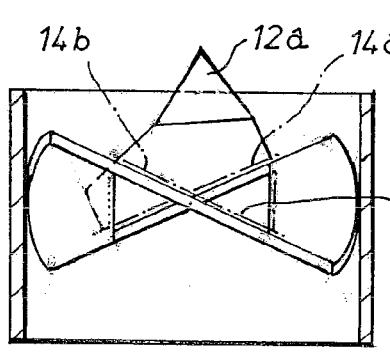
FIG. 4 is a side elevation of a second embodiment.
Figure 5:
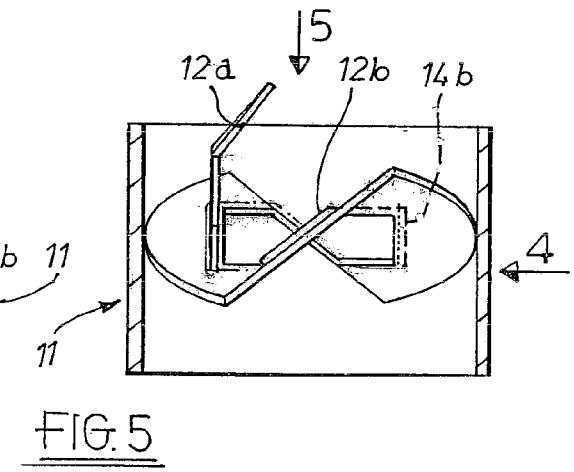
FIG. 5 is an elevation on Arrow 5 of FIG. 4.

The valve illustrated in FIGS. 4 to 6 has a pair of cooperating flaps 12a, 12b hinged on skew 14a, 14b hinges respectively and twisted to mate in the closed configuration and opening so that they form complementary flow-directing vanes. More complex flap valves, not shown, in accordance with the invention, have a plurality of cooperating flaps mating in an iris-like configuration and opening so as to form complementary flow-directing vanes, each having hinging inclined to the general flow direction.

Figure 7:
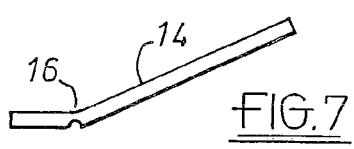
FIG. 7 is a section through flap material illustrating a first form of hinging.
Figure 8:
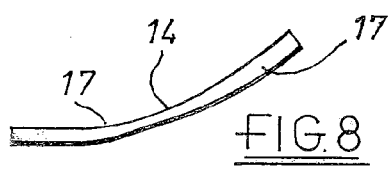
FIG. 8 is a section like FIG. 7 illustrating a second form of hinging.

Different methods of hinging are illustrated in FIGS. 7 and 8. FIG. 7 illustrates hinging 14 comprising a defined hinge line 16 formed by a linear thinned portion of flap material, while FIG. 8 illustrates hinging 14 comprising a thin flexible region 17 of flap material which arcs smoothly on opening.

Figure 9:
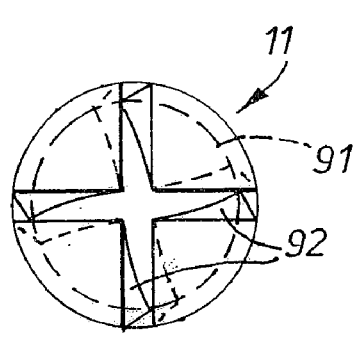
FIG. 9 is a side elevation of a third embodiment.
Figure 10:
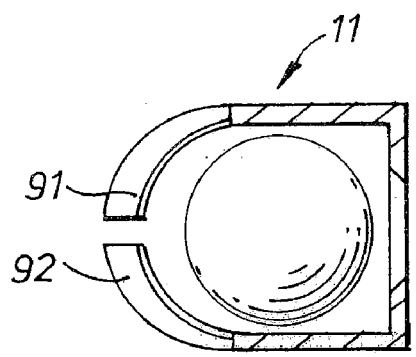
FIG. 10 is a view on Arrow 10 of FIG. 9.

FIGS. 9 and 10 illustrate a ball valve 11 which has a valve seat 91 comprising vane means 92 having a helical configuration. As shown, there are four vanes 91, though, of course, three would suffice and more than four would be possible. The ball 93 is movable within a cage formed partially by the vanes 92 and is forced away from the vanes 92 by pressure of blood entering the valve through the vanes 92 and is forced back by a resilient member, not shown, between the ball and the downstream retaining ring of the cage.

The helical flow induced by the flap or vane means in the various embodiments can be arranged, by suitable choice of the configuration, to reduce turbulence and/or dead flow regions in the bloodstream local to the valve. Care will clearly be taken not to introduce any such adverse flow characteristics by attention to streamlining of all components of the valve.

As mentioned above, whilst the avoidance of turbulence and dead flow regions has recently become of significance in the prevention of vascular problems leading to heart attacks and strokes, hence the description herein particularly of heart valves, the reduction of such adverse flow characteristics in other flow systems can also be important, and valves may be made after the fashion of the heart valves above described for such systems as chemical engineering plant, fuel pipelines and laboratory equipment.

And, while the valves above described are all one-way or check valves and passive inducers of helical flow, controlled, e.g. solenoid controlled or actuator controlled, valves may be configured for helical flow, and active inducement can be contemplated. For example, a ball valve which is electromagnetically operated my also have a rotating ball, rotated, say, by electromagnetic induction, which will induce helical flow and which has the additional advantage of being controllable as to the amount of helical component is to be induced, simply by controlling the rate of revolution of the ball.

The invention claimed is:

1. An apparatus comprising:
   (a) a heart valve prosthesis comprising:
   (i) a valve for inducing a helical flow pattern in blood exiting the valve, such as to substantially reduce or eliminate turbulence and dead flow regions in the blood flow, wherein the valve comprises:
   (I) a single flap having hinging, the single flap, when open, adopting a helical formation.

2. An apparatus according to claim 1, having an internal helical formation.

3. An apparatus according to claim 1, being a flap valve.

4. An apparatus according to claim 1, in which the hinging comprises a defined hinge line formed as a linear, thin, flexible portion of flap material.

5. An apparatus according to claim 1, in which the hinging comprises a thin flexible region of flap material which arcs smoothly on opening.

* * * * *